(12) United States Patent
Wiggins et al.

(10) Patent No.: US 7,619,413 B2
(45) Date of Patent: Nov. 17, 2009

(54) TRANSMIT-RECEIVE ARRAY FOR HIGH FIELD MRI

(75) Inventors: Graham Charles Wiggins, Lynn, MA (US); Lawrence Leroy Wald, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 139 days.

(21) Appl. No.: 11/839,094

(22) Filed: Aug. 15, 2007

(65) Prior Publication Data

US 2007/0282194 A1    Dec. 6, 2007

Related U.S. Application Data

(63) Continuation-in-part of application No. 11/579,576, filed as application No. PCT/US2005/015342 on May 3, 2005.

(60) Provisional application No. 60/568,035, filed on May 3, 2004, provisional application No. 60/838,067, filed on Aug. 16, 2006.

(51) Int. Cl.
  *G01V 3/00* (2006.01)
(52) U.S. Cl. ......................... 324/318; 324/309; 324/322
(58) Field of Classification Search ......... 324/300–322, 324/200; 600/410, 411, 422, 423; 333/219–235
  See application file for complete search history.

(56) References Cited

U.S. PATENT DOCUMENTS

| | | | |
|---|---|---|---|
| 4,825,162 A | 4/1989 | Roemer et al. | |
| 6,396,273 B2 | 5/2002 | Misic | |
| 6,534,983 B1 * | 3/2003 | Boskamp et al. | 324/318 |
| 6,946,840 B1 | 9/2005 | Zou et al. | |
| 6,989,673 B2 | 1/2006 | Zhu | |
| 7,394,251 B2 * | 7/2008 | Lin | 324/309 |
| 7,449,888 B1 * | 11/2008 | Malik et al. | 324/318 |
| 2002/0156362 A1 | 10/2002 | Bock et al. | |
| 2003/0100826 A1 | 5/2003 | Savelainen | |
| 2007/0013377 A1 * | 1/2007 | Wosik et al. | 324/322 |
| 2007/0282194 A1 * | 12/2007 | Wiggins et al. | 600/422 |
| 2008/0007250 A1 * | 1/2008 | Wiggins | 324/200 |
| 2008/0012564 A1 * | 1/2008 | Lin | 324/309 |

FOREIGN PATENT DOCUMENTS

WO    WO 2004038431 A2 *    5/2004
WO    WO 2005109010 A2 *    11/2005

OTHER PUBLICATIONS

B. Wu, X Zhang, G. X. Shen, An Optimized Four-Channel Microstrip Loop Array 7T, Proc. Intl. Soc. Mag. Reson. Med. 14 (2006), p. 2569.

(Continued)

*Primary Examiner*—Brij B. Shrivastav
*Assistant Examiner*—Tiffany A Fetzner
(74) *Attorney, Agent, or Firm*—Quarles & Brady LLP

(57) ABSTRACT

A multi-element MRI head coil is formed in the shape of a helmet that fits over the head of a subject to be imaged. The coil elements are separately driven by rf transmit channels during an MR scan to shape the rf fields produced in the region of interest. The head coil can be used in the transmit only phase of the scan, or it can be used in both the transmit and receive phases.

9 Claims, 6 Drawing Sheets

OTHER PUBLICATIONS

N. I. Avdievich, H. H. Hetherington, Improved Homogeneity of the Transmit Field due to Simultaneous Transmission with Phased Arrays and Volume Coils, Proc. Intl. Mag. Reson. Med. 14 (2006), p. 2567.

W. Driesel, C. J. Wiggins, G. C. Wiggins, L. L. Wald, T. Mildner, H.E. Moller, A Helmet Coil with Reduced Out-of-Volume Sensitivity for Human Brain Imaging at 7T, Proc. Intl. Soc. Reson. Med. 14 (2006), p. 3549.

C. Wang, G. X. Shen, Optimization of a Multi-Channel Transmit, Quadrature Receive Birdcage Coil, Proc. Intl. Soc. Mag. Reson. Med. 14 (2006), p. 3539.

A. Weisser, T. Lanz, A Volume Head Array with 8 Transmit/Receive Channels for 7T, Proc. Intl. Soc. Mag. Reson. Med. 14 (2006), p. 2591.

R. G. Pinkerton, J. P. Near, E. A. Barberi, R. S. Menon, R. Bartha, A Transceive Surface Coil Array for MRI of the Human Prostate at 4T, Proc. Intl. Soc. Mag. Reson. Med. 14 (2006), p. 2588.

R. G. Pinkerton, G. C. McKinnon, R. S. Menon, Sense-Optimization of a Transceive Surface Coil Array for MRI at 4T, Proc. Intl. Soc. Mag. Reson. Med. 14 (2006) p. 2584.

W. Driesel, T. Wetzel, T. Mildner, C. J. Wiggins, H. E. Moller, A Four-Channel Transceive Phased-Array Helmet Coil for 3T, Proc. Intl. Soc. Mag. Reson. Med. 14 (2006), p. 2583.

Y. Zhu, R. Watkins, R. Giaquinto, C. Hardy, G. Kenwood, S. Mathias, T. Valent, M. Denzin, J. Hopkins, W. Peterson, B. Mock, Parallel Excitation on an Eight Transmit-Channel MRI System, Proc. Int. Soc. Mag. Reson. Med. 13 (2005), p. 14.

Y. Li, C. Saylor, G. R. Duensing, Transmit Coil Array for Very High Field Head Imaging, Proc. Intl. Soc. Mag. Reson. Med. 14 (2006), p. 2564.

H. Nam, W. Grissom, S. M. Wright, Application of RF Current Sources in Transmit Sense, Proc. Intl. Soc. Mag. Reson. Med. 14 (2006), p. 2562.

C. J. Snyder, L. DelaBarre, C. Akgun, S. Moeller, G. Adriany, K. Ugurbil, J. T. Vaughan, High-Field Transmission Line Arrays for Transmit and Receive, Proc. Intl. Soc. Mag. Reson. Med. 14 (2006), p. 421.

Gregor Adriany, Pierre-Francois Van de Moortele, Florian Wiesinger, Steen Moeller, John P. Strupp, Peter Andersen, Carl Snyder, Xiaoliang Zhang, Wei Chen, Klaas P. Pruessman, Peter Boesiger, Tommy Vaughn, Kamil Ugurbil, Transmit and Receive Transmission Line Arrays for 7 Tesla Parallel Imaging, Magnetic Resonance in Medicine 53:434-445 (Feb. 2005).

G. C. Wiggins, C. J. Wiggins, A. Potthast, V. Alagappan, O. Kraft, A. Reykowski, L. L. Wald, A 32 Channel Receive-Only Head Coil and Detunable Transmit Birdcage for 7 Tesla Brain Imaging.

G.C. Wiggins, C. Triantafyllou, A. Potthast, A. Reykowski, N. Nittka, L.L. Wald, A 32 Channel Receive-Only Phased Array Head Coil for 3T with Novel Geodesic Tiling Geometry, Proc. Intl. Soc. Mag. Reson. Med. 13 (2005).

G.C. Wiggins, A. Potthast, C. Triantafyllou, F. Lin, T. Benner, C.J. Wiggins, L. Wald, A 96 Channel MRI System with 23- and 90-channel Phase Array Head Coils at 1.5 Tesla, Proc. Intl. Soc. Mag. Reson. Med. 13 (2005).

* cited by examiner

TRANSMIT-RECEIVE ARRAY FOR HIGH FIELD MRI

CROSS-REFERENCE TO RELATED APPLICATIONS

This application is based on U.S. Provisional Patent Application Ser. No. 60/838,067 filed on Aug. 16, 2006 and entitled "Transmit-Receive Array For High Field MRI," and it is a continuation-in-part of U.S. patent application Ser. No. 11/579,576 filed Nov. 2, 2006, which claims the benefit of International Application No. PCT/US2005/015342 filed on May 3, 2005 and U.S. Provisional Application No. 60/568,035, filed May 3, 2004.

STATEMENT REGARDING FEDERALLY SPONSORED RESEARCH

This invention was made with Government support under Grant No. RiR014075 awarded by the National Institute of Health. The Government has certain rights in the invention.

BACKGROUND OF THE INVENTION

The field of the invention is nuclear magnetic resonance imaging methods and systems. More particularly, the invention relates to rf coil systems for applying an excitation field to a subject under examination.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment Mt. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

At high fields (>1.5T) wavelength effects cause the transmit RF field ($B_1$ field) in the human body to be inhomogeneous. In head imaging, the $B_1$ field is typically highest in the center of the head, and significantly lower in the temporal lobes and cerebellum. At 7 Tesla, the $B_1$ field in the temporal lobes is typically about 50% of that in the center of the head. This causes variations in contrast over the head in MR imaging, and results in lower SNR in regions with low $B_1$ field. Body imaging at 3T and above suffers from similar inhomogeneities in the $B_1$ field.

There is at present no simple solution to the problem of $B_1$ inhomogeneity in high field MRI. Various methods have been proposed and demonstrated to various degrees. One approach proposed by researchers from Siemens involves using a separate surface coil tuned off-resonance (not detuned, but tuned to a higher frequency) which was placed on the abdomen in a 3T scanner to increase the $B_1$ field in an area where it was otherwise relatively low. Placing bags of water or ultrasound gel around the head has been shown to change the $B_1$ field within the head. Controlling the phase and amplitude of individual rungs in a birdcage type transmit coil has been shown in modeling to change the $B_1$ field and make possible greater homogeneity, but practical demonstrations have not fully realized the theoretical results. Shaped RF pulses when applied concurrently with appropriate magnetic field gradients can be used to compensate for $B_1$ inhomogeneity, but the pulses are very long and not practical for most uses. The use of accelerated transmit techniques (sometimes referred to as Transmit SENSE) with a transmit array reduces the length of the shaped RF pulse to a more practical level, and this is currently a topic being studied by many groups. Transmit array designs to date have largely consisted of a number of coil elements on a cylindrical form arranged azimuthally around the head with no distribution of elements along the Z-direction.

SUMMARY OF THE INVENTION

The present invention is an MR coil array comprised of a plurality of tuned coil elements arranged around a sample or living subject which can be driven with a corresponding plurality of RF signals to produce the desired distribution of RF energy in the sample or living subject. In particular, through control of the phase and amplitude of the RF signal sent to each coil element, or with the implementation of Transmit SENSE, the invention can be used to create a more uniform $B_1$ field than is currently possible in high field MRI, or to produce focused RF excitation of particular regions of interest to reduce the overall SAR load.

The tuned coil elements are arranged around the sample or living subject in a 3D distribution surrounding as much as possible of the object. Each coil element has a spatially distinct excitation and reception profile, and these profiles are arranged in such a way that there are separate overlapping profiles in all directions, including along the Z direction.

The invention is used in connection with high field (>1.5T) MRI scanners. It may be embodied in a helmet-shaped substrate covered with surface coil elements each of which can both transmit and receive an RF signal at the operating frequency of the MRI scanner. It may also be embodied in a larger helmet-like structure having an array of coil elements that only creates a transmit $B_1$ field and has separate receive coils within it. Such structures require additional hardware to separately control the RF signal fed to each coil element, either by adjusting the phase and amplitude of the signal to each element or by sending different RF waveforms to each element as with Transmit SENSE. The device allows greater homogeneity of the $B_1$ field in high field MRI, or it allows focused RF excitation of only particular regions of interest to reduce the overall SAR load in the subject.

DESCRIPTION OF THE PREFERRED EMBODIMENT

Figure 1:
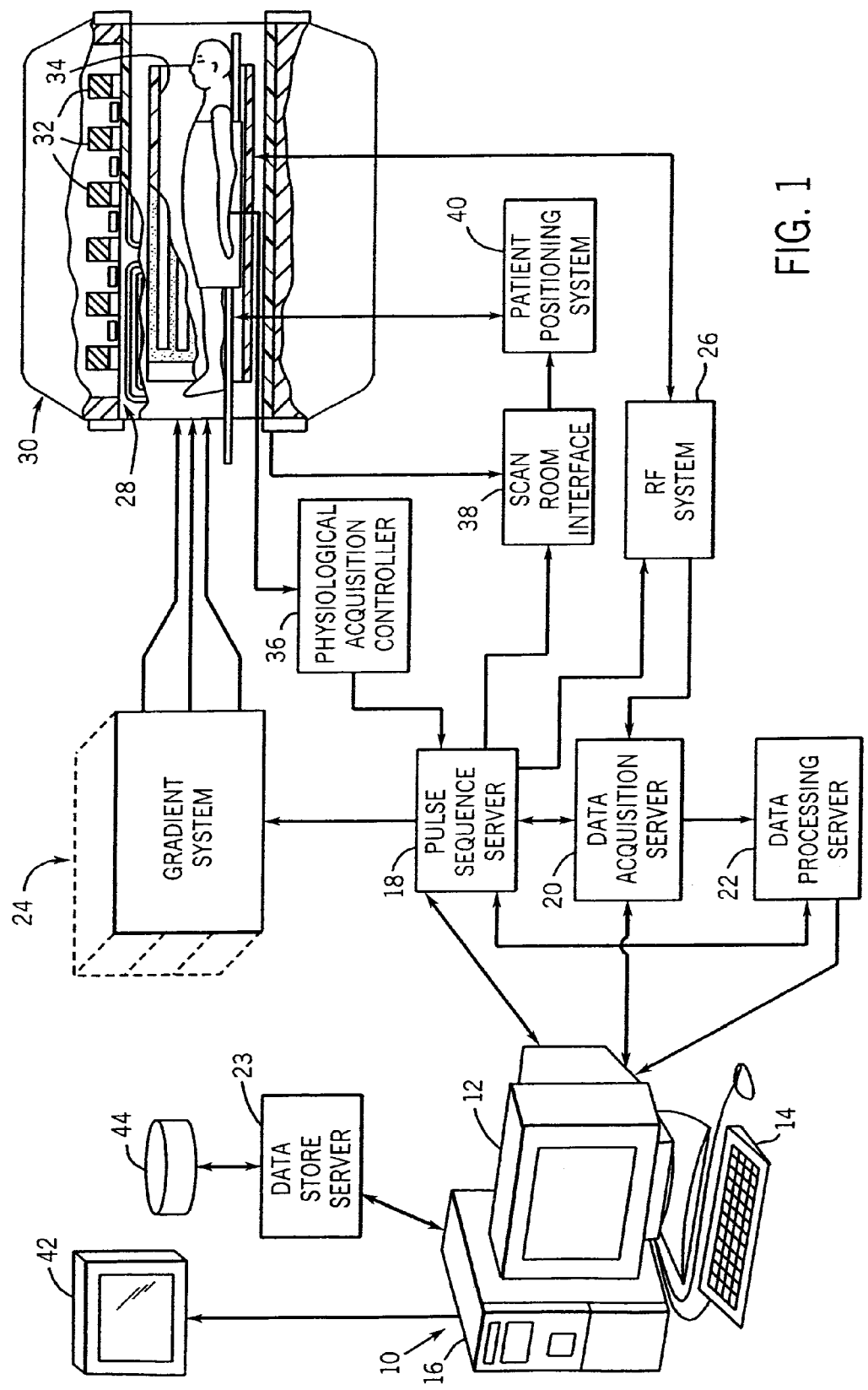
FIG. 1 is a block diagram of an MRI system which employs the present invention.

Referring particularly to FIG. 1, the preferred embodiment of the invention is employed in an MRI system manufactured by Siemens Medical Solution of Erlangen, Germany. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$, and $G_z$ used for position encoding NMR signals. The gradient coil assembly 28 forms part of a magnet assembly 30 which includes a polarizing magnet 32 and a whole-body RF coil 34.

RF excitation waveforms are applied by the RF system 26 to perform the prescribed magnetic resonance pulse sequence. Responsive NMR signals detected by a separate RF coil array described below are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. As will be described in more detail below, when used to practice the present invention the RF transmitter has a plurality of separately controlled transmit channels and their outputs are coupled to the RF coil array described below.

The RF system 26 also includes a plurality of RF receiver channels. In the preferred embodiment 80 receiver channels are employed although any number of receive channels may be employed depending on the receive coil array being used. Each RF receiver channel includes an RF amplifier that amplifies the NMR signal received by the coil to which it is connected.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with an image reconstruction method. Images reconstructed by the data processing server 22 are conveyed back to the workstation 10 where they are stored. Real-time images may be output to operator display 12 or a display 42 which is located near the magnet assembly 30 for use by attending physicians. Batch mode images or selected real time images are stored in a host database on disc storage 44. The workstation 10 may be used by an operator to archive the images, produce films, or send the images via a network to other facilities.

Figure 2:
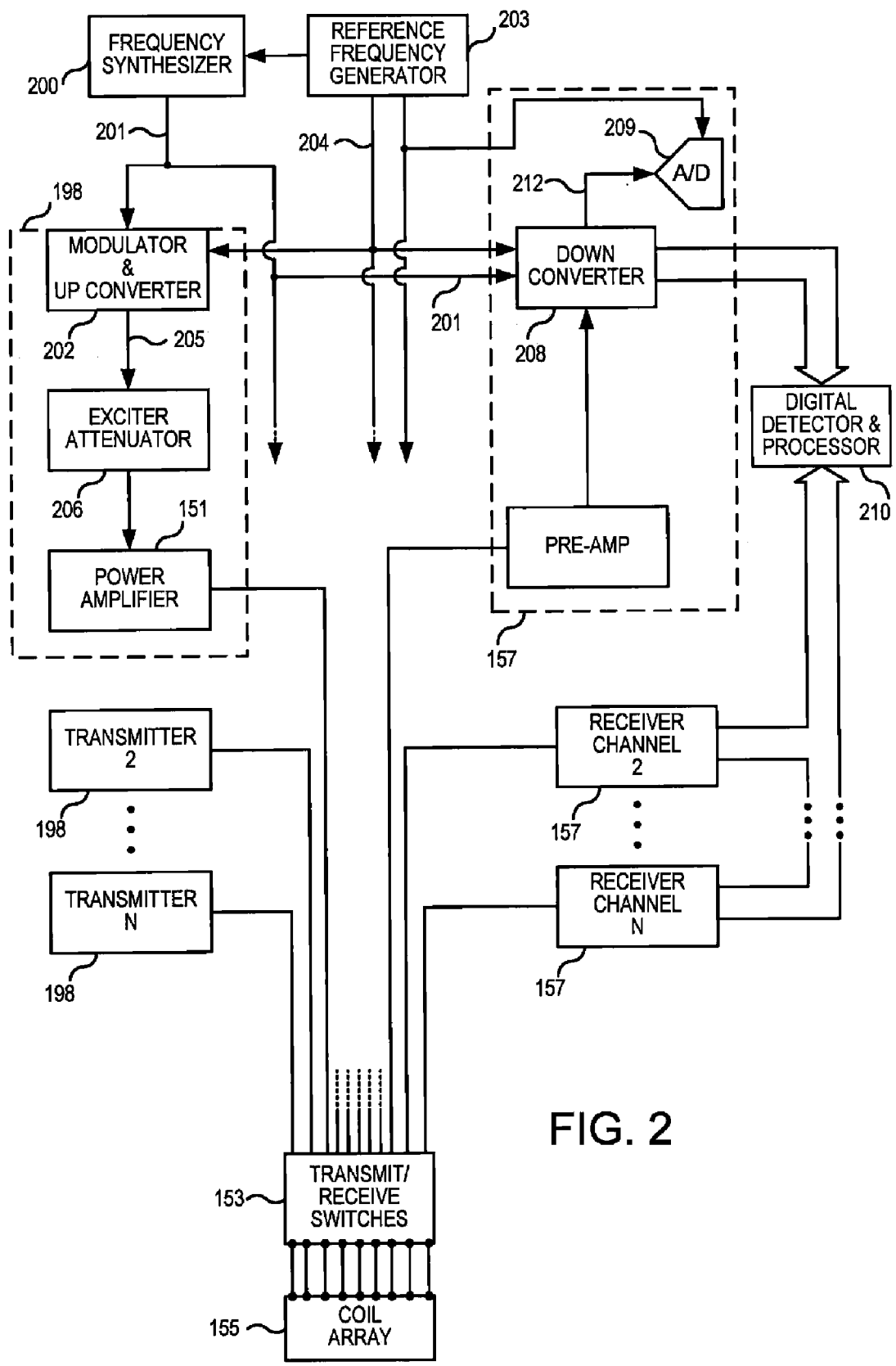
FIG. 2 is a block diagram of a transceiver which forms part of the MRI system of FIG. 1.

Referring particularly to FIG. 2, the RF system 26 includes a set of transmitters 198 that each produce a prescribed rf excitation field. The base, or carrier, frequency of this RF excitation field is produced under control of a frequency synthesizer 200 which receives a set of digital signals from the pulse sequence server 18. These digital signals indicate the frequency and phase of the RF carrier signal produced at an output 201. The RF carrier is applied to a modulator and up converter 202 in each transmitter 198 where its amplitude is modulated in response to a signal R(t) also received from the pulse sequence server 18. The signal R(t) defines the envelope, or waveform, of the RF excitation pulse to be produced and is produced by sequentially reading out a series of stored digital values. These stored digital values maybe changed to enable any desired RF pulse envelope, or waveform, to be produced by each transmitter 198. The RF pulses produced by the transmitters 198 can thus be separately controlled by the pulse sequence server 18. The phase and amplitude of the separate RF fields can be controlled to achieve $B_1$ shimming and the waveforms can be shaped and played out simultaneously with gradient waveforms to implement Transmit SENSE.

The magnitude of the RF excitation pulse produced at output 205 is attenuated by an exciter attenuator circuit 206 in each transmitter which also receives a digital command from the pulse sequence server 18. The attenuated RF excitation pulses are applied to a power amplifier 151 in each transmitter 198. The power amplifiers may be current source devices that connect to respective transmit inputs on a set of transmit/receive switches 153. In the first preferred embodiment eight transmitters 198 are employed and connected through eight transmit/receive switches 153 to eight coil elements in a coil array 155.

Referring still to FIG. 2 the signal produced by the subject is picked up by the coil array 155 and applied to the inputs of a set of receive channels 157. A pre-amplifier 160 in each receiver channel 157 amplifies the signal by an amount determined by a digital attenuation signal received from the pulse sequence server 18. The received signal is at or around the Larmor frequency, and this high frequency signal is down converted in a two step process by a down converter 208 which first mixes the NMR signal with the carrier signal on line 201 and then mixes the resulting difference signal with a reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

The transmit/receive switches 153 are operated by the pulse sequence server 18 to connect the N=8 transmitters 198 to the N=8 coil elements in the coil array 155 during those parts of the pulse sequence in which an rf magnetic field is to be produced. Each transmitter 198 is separately controlled by the pulse sequence server 18 to produce an rf field of a prescribed amplitude, frequency, phase and envelope at each of the N=8 coil elements. The combined rf fields of the N=8 coil elements produce the prescribed $B_1$ field throughout the region of interest in the subject being imaged. Each transmitter 198 is also separately controlled to play out a pulse envelope, or waveform, while driving the gradient coils with waveforms that implement Transmit SENSE.

When the $B_1$ field is not produced the pulse sequence server 18 operates the transmit/receive switches 153 to connect each of N=8 receive channels to the respective N=8 coil elements. Signals produced by excited spins in the subject are picked up and separately processed as described above.

Figure 3:
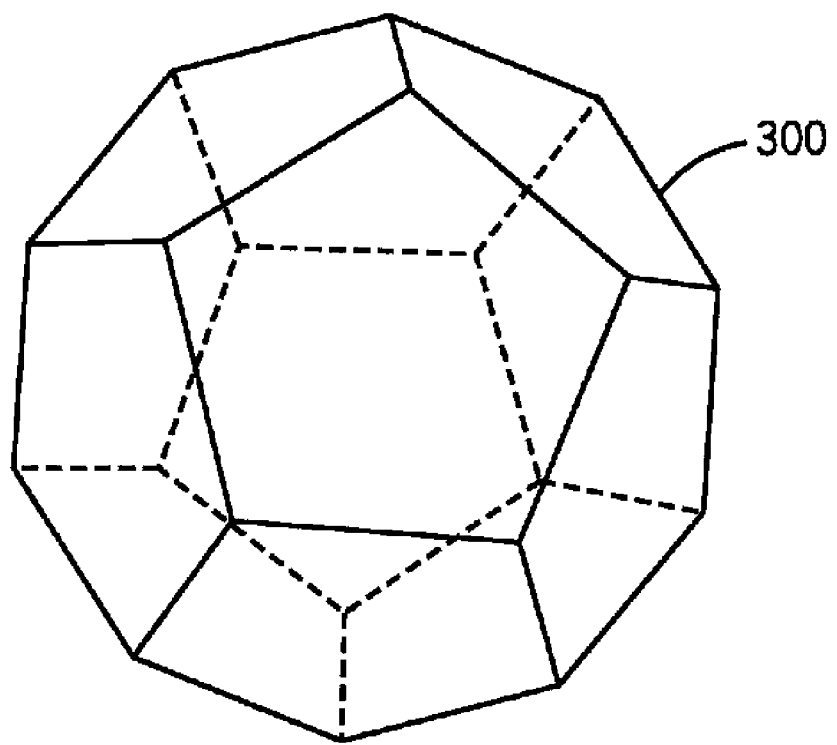
FIG. 3 is a line drawing of a dodecahedron shape which forms the basic shape of a first embodiment of the coil array of the present invention.
Figure 4A:
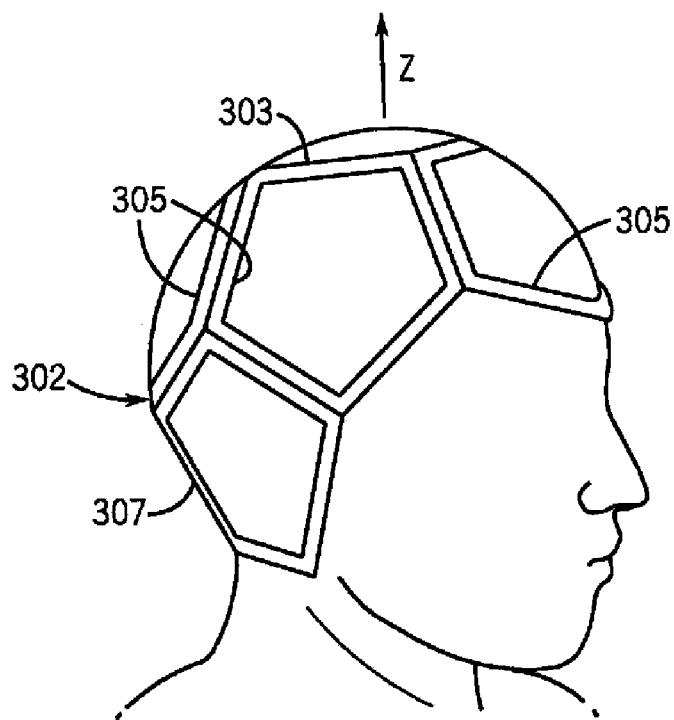
FIGS. 4A and 4B are pictorial views of the first embodiment of the coil array seen from two different view angles.
Figure 4B:
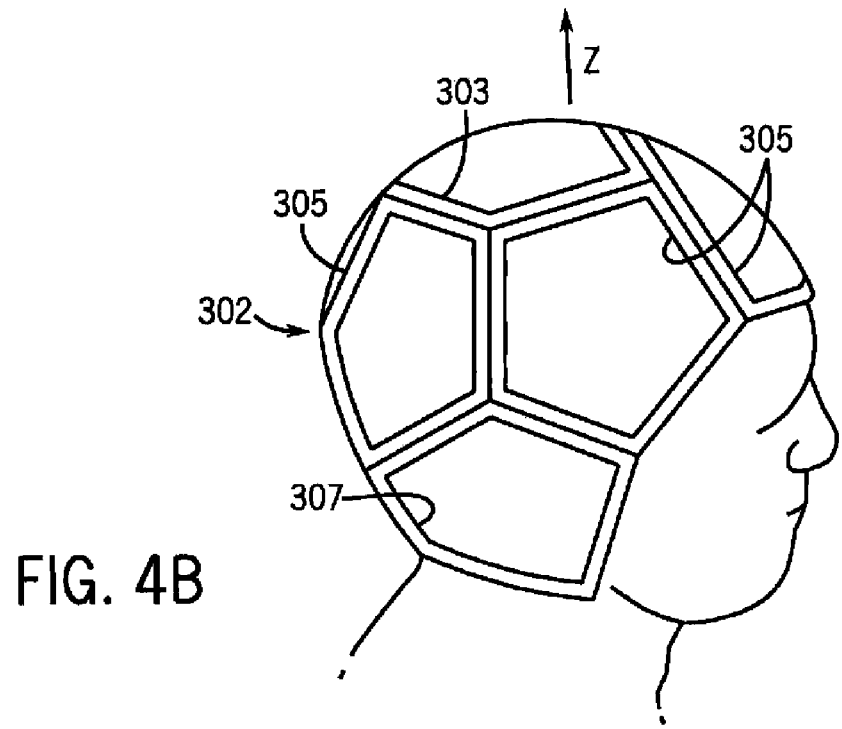

In the preferred embodiment of the invention the coil array 155 includes only N=8 coil elements. As shown in FIGS. 3, 4A, and 4B, a helmet-shaped array of coil elements is formed based on 12 identical pentagonal faces of a dodecahedron 300. Four of the pentagonal faces are left off the dodecahedron 300 to form a helmet 302 as shown in FIGS. 4A and 4B which fits over the head of a subject being imaged. With a coil element 303 on the apex of the head, with five coils 305 surrounding the top of the head and with two coils 307 at the back of the head, there are three layers in the Z-direction, allowing SENSE acceleration (receive or transmit) in any direction.

Figure 5A:
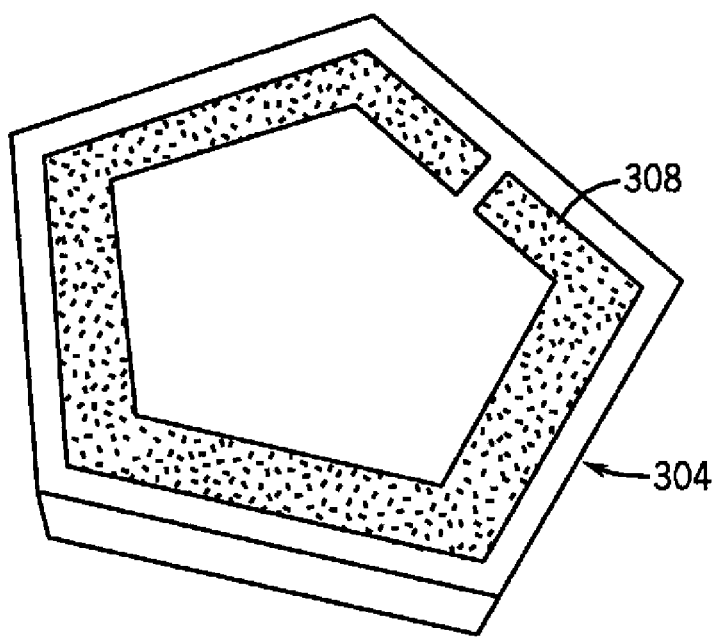
FIGS. 5A and 5B are two pictorial views of the coil element in the coil array of FIG. 4.
Figure 5B:
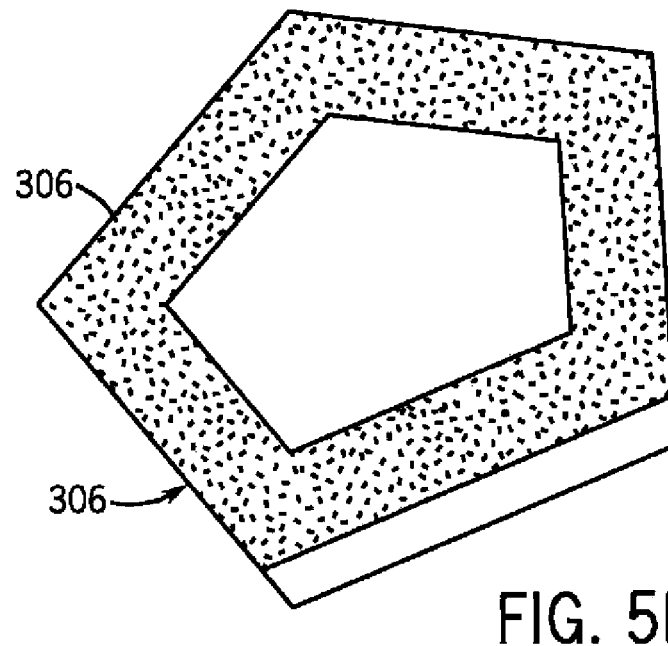

Each coil element is formed as a stripline loop coil 304 having a pentagonal shape as shown in FIGS. 5A and 5B. On the back side of the coil element 304 is a ground plane 306 and on the front side is an active loop 308. The pentagonal coil elements 304 are assembled into the dodecahedral structure with small gaps between them. Capacitive decoupling is needed between neighboring coil elements 304, but coupling between next nearest neighbors is very weak with a stripline coil.

In the preferred embodiment described above, the N=8 coil elements are used for both RF transmission and reception of the MR signals. It should be apparent that this coil array 302 may also be used for RF transmission only and a separate receive-only coil array may be used for reception of the MR signals. This may be done, for example, when the MRI system has only 8 transmit channels, but it has a much larger number of receive channels. In this case, the receive coil array is disposed inside the transmit coil array where it is as close as possible to the subject being imaged. A helmet coil array such as that now to be described may be used for this purpose and the 8-element transmit coil array 302 may be formed on an outer, slightly larger shell.

Figure 6:
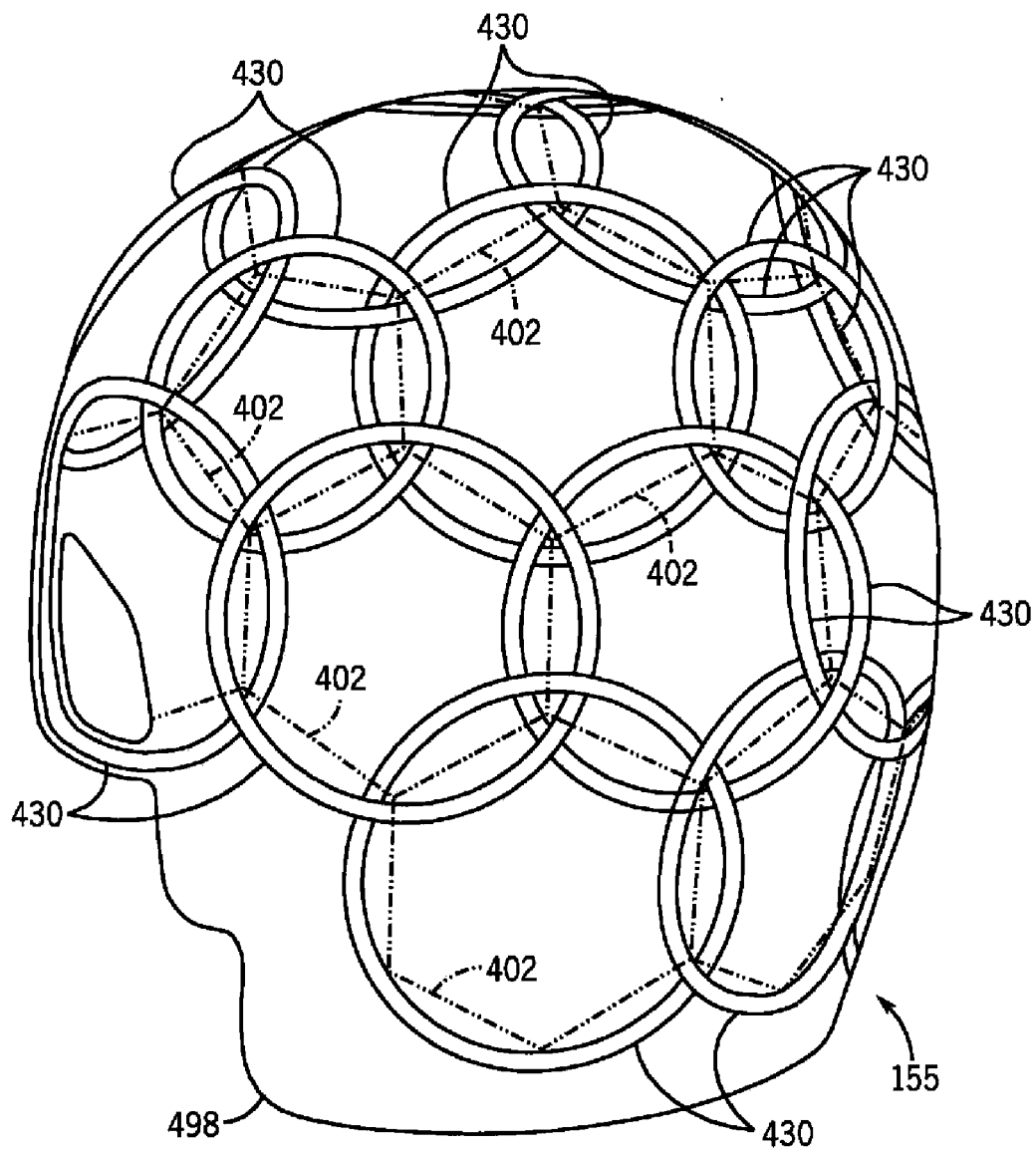
FIG. 6 is a perspective view of a second embodiment of a coil array for use with the transceiver of FIG. 2.

With the availability of more independent transmit channels, transmit-receive arrays with much higher numbers of elements is preferred. Such an alternative embodiment of the coil array 155 is shown in FIG. 6. This coil array 155 has a much larger number of separate rf coil elements which are positioned over the curved helmet surface. Each coil element is substantially circular in shape and adjacent coil elements overlap such that their mutual inductance is minimized.

The preferred coil array 155 in FIG. 6 is formed in the shape of a helmet 498 that is placed on the head of a subject. It is used for MR brain imaging. The close-fitting fiberglass helmet 498 is modeled after the European head standard form EN960/1994 for protective headgear. This coil array 155 has separate rf coil elements 430 which are supported by the curved helmet surface that acts as a substrate. Each coil element is substantially circular in shape and adjacent coil elements overlap such that their mutual inductance is minimized. An arrangement of hexagonal and pentagonal tiles (indicated by dashed lines 402 in FIG. 6) cover the helmet surface, similar to a truncated icosahedron or "soccer ball." This structure has been found to maintain the critical overlap between adjacent coil elements that minimizes their mutual inductance. Each tile 402 has sides that are approximately 40 mm long and a circular surface coil 430 is centered on each one of the tiles 402. Each surface coil 430 is made from Pyralux flexible circuit board with a conductor width of 5 mm. The diameter of each coil element ranges from 8.5 cm to 6.0 cm. It has been found that significant 5 to 8-fold gains in SNR are possible with this structure as compared to conventional head coils, particularly in the cerebral cortex. This embodiment is preferred for head coils having from 8 to 56 coil elements 430, whereas coil elements constructed of circular-shaped wire is preferred for head coils having more than 56 coil elements 430.

The technology of receive coil arrays is well developed as described above, and relies on the techniques of preamp decoupling, which reduces coupling between coil elements by minimizing the currents which can flow in the coil elements. This technique cannot be applied in the case of a transmit coil array because a flow of current in the coil elements is necessary to create a $B_1$ field with the device. This means that coupling between the coil elements is much more problematic in a transmit array. One of the main techniques for reducing coupling between coil elements is to overlap them to null their mutual inductance. Our soccer-ball type coil design allows the critical overlap to be maintained between all neighboring coils even for a domed design which conforms closely to the shape of the human head. Coupling between neighboring coils can also be minimized through the use of capacitive or inductive decoupling networks. Coupling between any coil pair during transmit (including non-neighboring coils) can also be reduced through the use of current source amplifiers 151 for each element. Also, the use of shielded or "stripline" coil elements may be used to reduce coupling between coil elements.

Distributing the coil elements all over the surface of the head provides greater flexibility in controlling the $B_1$ field created by the coil, either through adjustment of the waveform, phase and amplitude of the RF signal sent to each element, or through the use of different coil elements over the surface of the head to allow Transmit SENSE acceleration in any chosen direction. The soccer-ball-type geometries and the principle of arranging the elements close to the head with an even spatial distribution in all directions improves $B_1$ shimming and Transmit SENSE applications regardless of the design of the individual elements and the decoupling methods used.

The invention claimed is:

1. A transmit coil array, operating in a high magnetic field strength environment of greater than 1.5 Tesla, configured for use with an MRI system having a plurality of parallel separately controllable rf transmitters, the combination comprising:
   a transmit coil array having a plurality of separate coil elements, each coil element configured to be coupled to a respective one of the rf transmitters via parallel separately controllable transmit channels and the coil elements being configured to surround an anatomical region of interest; and
   wherein a pulse generator is operable in order to separately and independently control each of the plurality of rf transmitters such that the transmit coil array produces a prescribed B1 rf field in the anatomical region of interest.

2. The transmit coil array as recited in claim 1 in which the prescribed B1 rf field is substantially homogeneous throughout the anatomical region of interest.

3. The transmit coil array as recited in claim 1 in which the transmit coil array is shaped in order to contour around the head of a human subject.

4. The transmit coil array of claim 3, in which the transmit coil array includes a helmet-shaped substrate and the coil elements are disposed over substantially all the surface of the helmet.

5. The transmit coil array as recited in claim 4 in which the coil elements overlap each other in order to reduce mutual inductance therebetween.

6. The transmit coil array as recited in claim 1 in which the rf transmitters each include a current source amplifier in order to reduce coupling between coil elements.

7. The transmit coil array as recited in claim 4 in which the helmet surface is divided into hexagonal and pentagonal tiles and a circular coil element is centered on each tile.

8. The transmit coil array as recited in claim 1 in which each coil element is also coupled to a respective one of a plurality of receive channels in the MRI system, whereby the transmit coil array is also a transmit-receive coil array.

9. The transmit coil array as recited in claim 3 in which there are eight coil elements and each has a pentagonal shape.

* * * * *